(12) United States Patent
Escaf (10) Patent No.: US 8,876,745 B2
(45) Date of Patent: Nov. 4, 2014

(54) STREAMLINED ULTRASONIC DEVICE AND METHOD OF USE

(75) Inventor: Luis Jose Escaf, Barranquilla (CO)

(73) Assignee: Alcon Research Ltd., Fort Worth, TX (US)

( * ) Notice: Subject to any disclaimer, the term of this patent is extended or adjusted under 35 U.S.C. 154(b) by 1004 days.

(21) Appl. No.: 12/409,198

(22) Filed: Mar. 23, 2009

(65) Prior Publication Data

US 2009/0247936 A1    Oct. 1, 2009

Related U.S. Application Data

(60) Provisional application No. 61/064,746, filed on Mar. 24, 2008.

(51) Int. Cl.
*A61B 17/20* (2006.01)
*A61F 9/007* (2006.01)

(52) U.S. Cl.
CPC .................................. *A61F 9/00745* (2013.01)
USPC ........................................................... 604/22

(58) Field of Classification Search
CPC .................................................. A61F 9/00745
USPC ...................................... 604/20–23; 606/169
See application file for complete search history.

(56) References Cited

U.S. PATENT DOCUMENTS

| | | | |
|---|---|---|---|
| 3,589,363 A | | 6/1971 | Banko et al. |
| 5,527,273 A | * | 6/1996 | Manna et al. .................... 604/22 |
| 5,718,676 A | | 2/1998 | Barrett |
| 7,588,553 B2 | * | 9/2009 | Dewey ............................ 604/22 |
| 2004/0199171 A1 | | 10/2004 | Akahoshi |
| 2004/0199192 A1 | | 10/2004 | Akahoshi |
| 2006/0047254 A1 | | 3/2006 | Akahoshi |
| 2007/0060926 A1 | | 3/2007 | Escaf |

* cited by examiner

*Primary Examiner* — Kami A Bosworth
*Assistant Examiner* — Imani Hayman
(74) *Attorney, Agent, or Firm* — Smith, Gambrell & Russell LLP (57) ABSTRACT

A phacoemulsification device has a cutting tip for insertion into an eye and contact with a cataract. The device includes a shaft having a phacoemulsification movement generator connector end, an applicator tip supporting end, and a shaft section extending between the respective ends of the shaft. The shaft section has a convoluted exposed surface comprising longitudinally extending projections and longitudinally extending valleys arranged in sequence about the circumference of the shaft section. The projections are free of any edges as in, for example, an embodiment that includes projections and valleys that have smooth sloped curving walls in cross section and include a plurality of mirror image S-shaped regions extending from a maximum radial extension of a first projection, down to a maximum depth of a first valley and up to a maximum radial extension of a second projection, with the valley positioned between the first and second projections.

30 Claims, 5 Drawing Sheets

STREAMLINED ULTRASONIC DEVICE AND METHOD OF USE

BENEFIT CLAIM(S)

This application claims the benefit of U.S. Provisional Application No. 61/064,746, filed Mar. 24, 2008, which application is incorporated herein by reference in its entirety.

FIELD OF THE INVENTION

The invention relates to an ultrasonic instrument as in a phacoemulsification device. An example is seen in a phacoemulsification device with a cutting tool tip and an aspiration passageway which provides an opthalmologic surgery cutting device well suited for cataract removal. The invention also pertains to surgical instruments and techniques comprising the ultrasonic instrument. In an exemplary embodiment the surgical instrument is a streamlined phacoemulsification opthalmologic surgical instrument that can be used free of a cooling fluid outer sleeve based on a high heat exchange elongated shaft or stem. An exemplary embodiment features a phacoemulsification device with a high heat exchange stem supporting a phaco tip that provides for dividing cataracts into more manageable fragments and which can be inserted into an eye incision that is small (e.g., less than or equal to a 1.5 mm incision as in 1.0+/−0.2 mm).

BACKGROUND OF THE INVENTION

Reference is made to US Publication 2007/0060926 to Luis J. Escaf (the present inventor) published Mar. 15, 2007; U.S. Pat. No. 3,589,363 to Banko et al. which issued Jun. 29, 1971, U.S. Pat. No. 5,718,676 to Barrett which issued on Feb. 17, 1988 as well as US Publication 2006/0047254 to Akahoshi which published Mar. 2, 2006 and all of which are incorporated herein by reference for background purposes.

SUMMARY OF ILLUSTRATIVE EXEMPLARY EMBODIMENTS

An embodiment includes a phacoemulsification device that comprises a shaft having a proximal end and a distal end and an applicator tip provided at the distal end. The shaft including an aspiration passageway extending within the shaft and the applicator tip having an aspiration port that is in flow communication with the aspiration passageway, and the shaft further includes a shaft section having an exposed convoluted surface that extends longitudinally along the shaft section and, in cross-section, has, for example, a sinusoidal pattern.

An embodiment features a shaft section's convoluted surface that includes a plurality of longitudinally elongated valleys each with a concave base surface section and which valleys are placed to opposite sides of a plurality of longitudinally extending projections, with each projection having a convex outermost surface section. An exemplary embodiment includes a convoluted exposed surface that has the curvature of the convex outermost surface section of at least some of the projections equal to the curvature of the concave base surface section of at least some of the valleys.

An additional embodiment example features an arrangement wherein two times a radius value for the concave base surface curvature is equal to the maximum depth of each valley down from a circumferential line which contacts the outermost points of the projections. An additional example features longitudinally elongated valleys and projections that are linearly arranged as to extend parallel to a central axis of extension of said shaft section, and with the aspiration passageway extending along that central axis of extension.

An embodiment includes a shaft section that has a base body with an interior surface defining the aspiration passageway and an exterior surface which defines the radially interior most points of the concave base surface sections of the valleys, and the projections extend radially off the base body to about an equal amount or greater extent than the radial thickness of the base body.

As an additional embodiment example, the exposed convoluted surface of the shaft section is configured as to be free of any sharp edge presentations along the entire length of the exposed convoluted surface, whereas an additional embodiment avoids sharp edges in each of the valleys as well as in the projections, as in the entire exposed surface of the shaft section being free of any sharp edges about the circumference of the shaft section (e.g., there may be a sharp edge at the border of the shaft section where the extreme ends of the valleys exist, while in an alternate embodiment there is further provided a smooth rise and curved border region at that step down between the shaft section and remaining portion of the shaft itself).

An embodiment includes a circumferential width of an intermediate in height region of at least some of the projections being about equal to the circumferential width of an adjacent valley of that projection. An additional embodiment example includes an arrangement wherein all of the projections have a common cross-sectional configuration about the entire circumference of the shaft section and all of the valleys have a common cross-sectional configuration about the entire circumference of the shaft section.

An alternate embodiment features an arrangement wherein the projections include a first set of projections and a second set of projections as in one where the first set of projections have a convex (e.g., generally semi-circular in cross section) outermost exposed surface presentation, and wherein projections of the second set of projections have an outermost exposed surface presentation that is circumferentially longer in cross-section than outermost cross-sectional exposed surface presentations presented by the projections in the first set, and preferably, for this embodiment, all projections in said first and second sets have curved side walls edge regions that extend down and away from the curved outermost exposed surface presentations of the respective projections.

A still further embodiment example includes an arrangement wherein the first set of projections includes projections that are positioned, when the device is in use, in both an upper and lower region of the exposed convoluted surface of the shaft section, and wherein the projections of the second set are positioned, when the device is in use, to left and right sides of the exposed convoluted surface of said section. For example, when the applicator tip is a cutting edge a vertical plane in which the cutting edge lies extends through the upper and lower regions where the first set of projections are provided while the second set of projections fall to opposite sides of that vertical plane.

An embodiment includes a first set of projections and a second set of projections with the first set of projections having a curved outermost exposed surface region, and wherein projections in the second set of projections have an outermost exposed surface region that is circumferentially longer than the curved outermost exposed surface regions presented by projections in said first set, and wherein all projections in said first and second sets have curved side walls edge regions that extend down and away from a radial outermost curved region of the respective projections. A further embodiment example further features the first set of projections having projections that are positioned, when the device is in use, in both an upper and lower region of the exposed convoluted surface of the shaft section, and wherein the projections of the second set are positioned, when the device is in use, to left and right sides of the exposed convoluted surface of the shaft section.

In yet another example, each set of projections has a configuration represented by taking a pair of projections in said first set of projections and an associated valley therebetween and filling in (conceptually and not necessarily in a process sequence) that associated valley up to the circumferential line that extends between radial outermost points of pair of projections in said first set of projections as to form a convex profile in the exposed outermost cross-section of each projection of the second set.

Also an embodiment includes a reference circumferential line extending into contact with a radial outermost point of those projections that is about 1 mm or less in diameter, and an aspiration passageway that is defined by an internal surface of the shaft section which has a radius of about 45% relative to the radius of the circumferential line, and wherein the shaft section is comprised of a base body off from which the projections radially extend outward, and the valleys having a maximum depth that represents about 55% of the radial distance from said internal surface to the circumferential line.

An embodiment of the invention includes a method of removing a cataract, comprising inserting an embodiment represented, for example, by the device embodiments described above, into an incision formed in an eye (e.g., the cornea or sclera) of less than 1.5 mm (e.g., about 1.2 mm or below) such that projections of the convoluted exposed surface come into direct contact with wall segments of the eye defining the incision, and wherein the device is subject to vibration.

A method embodiment further includes providing a cooling fluid irrigation source incision that is separate and apart from the device insertion incision, and wherein the device comprises a connection hub at the proximal end suited for attachment with a phacoemulsification movement generator. A suitable cooling fluid source can be inserted into the cooling fluid reception incision as by an independent fluid conduit member.

An additional embodiment features a phacoemulsification device having an applicator tip for insertion into an eye and into contact with a cataract as well as a shaft having a phacoemulsification movement generator connector end at a proximal location and an applicator tip supporting end at a distal end. The shaft also preferably includes in this embodiment a shaft section that extends in a region positioned between said proximal and distal ends of the shaft, and with that shaft section having a convoluted exposed surface which includes longitudinally extending projections (e.g., linearly or twisted or oblique arrangements as some examples of longitudinally extending valleys and longitudinally projections) with the valleys preferably being arranged in sequence (e.g., an equally spaced sequence) about the circumference of the shaft section, and wherein the projections and valleys have smooth sloped curving walls in cross section as in an arrangement wherein the projections and valleys have smooth sloped curving walls that include a plurality of mirror image S-shaped regions extending from a maximum radial extension region of a first projection, down to a maximum depth valley region of a first valley and up to a maximum radial projection of a second projection, with said valley region being positioned between respective first and second projections.

An additional example includes providing a convoluted support surface that has a diameter in cross-section that is about 1 mm or less, and with the shaft preferably including a longitudinally extending aspiration passageway, and a least one inlet port that is, for example, provided at the application tip and which is in fluid communication with the aspiration passageway extending in said shaft section.

An additional embodiment example includes a device that has an application tip in the form of a cutter tip with an opposing flat faced side walls section, and a pair of the at least one inlet ports being positioned to opposite sides of the flat faced walls section and extending in converging fashion into fluid communication connection with the aspiration passageway, and wherein, for example, the inlet ports converge into a common oblong cross sectioned coinciding outlet port portion that feeds directly into the aspiration passageway.

An embodiment of the convoluted exposed cross section of the shaft section includes one that is free of any sharp edge sections about the entire exposed cross-sectional surface presented by that shaft section region with projections and valleys. An additional embodiment includes one that has first set of projections and a second set of projections with said first set of projections having a curved outermost exposed surface region, and wherein projections in the second set of projections have an outermost exposed surface region that is circumferentially longer than the curved outermost exposed surface regions presented by projections in the first set, and wherein all projections in the first and second sets have curved side walls edge regions that extend down and away from a radial outermost curved region of the respective projections.

An additional exemplary embodiment includes one with a set of projections which include projections that present a semi-circular radially outermost region and with the first set of projections being positioned, when the device is in use, in both an upper and lower region of the exposed convoluted surface of the shaft section, and wherein the projections include a second set of projections that are positioned, when the device is in use, to left and right sides of the exposed convoluted surface of the shaft section.

An additional embodiment example includes one that is a phacoemulsification device that comprises an applicator tip with at least one aspiration port, a movement generator connector, and a shaft extending between the applicator tip and the movement generator connector. The shaft includes a shaft section with an internal aspiration pathway in fluid communication with the aspiration port, and which shaft section further comprises a convoluted exposed surface which includes longitudinally extending projections and longitudinally extending valleys arranged in sequence about the circumference of the shaft section, and wherein the projections have smooth sloped curving walls in cross section as to avoid sharp edge presentment about the circumference of the convoluted exposed surface of the shaft section. In addition there is preferably provided an embodiment having an arrangement wherein the valleys and the projections are entirely comprised of curved surface sections. There is also provided in an exemplary embodiment a device that comprises a phacoemulsificaton movement generator connected with the movement generator connector which is provided at the distal end of the shaft. A further embodiment example includes one where there is provided a first set of projections and a second set of projections with each set presenting an exposed convex surface at a radial outermost end, and with the projections of the first set having a smaller radius convex curvature as compared to the convex curvature of the second set of projections.

DETAILED DISCUSSION OF EXEMPLARY EMBODIMENTS

The illustrated embodiments depict a surgical instrument 20 as in a phacoemulsfication opthalmogic surgical instrument that is shown as comprising a preferably generally cylindrical, hollow shaft or stem supporting, at a distal end, a cutting and/or chopping tip with the figures showing a flattened tip preferably having fluid and debris access apertures as in one or more aspiration holes (e.g., one or more (preferably one) upper edge holes and/or one or more (preferably two opposite) side aspiration holes), with the illustrated embodiments depicting opposite side two holes, respectively, in communication with the bore of a hollow shaft.

Figure 1:
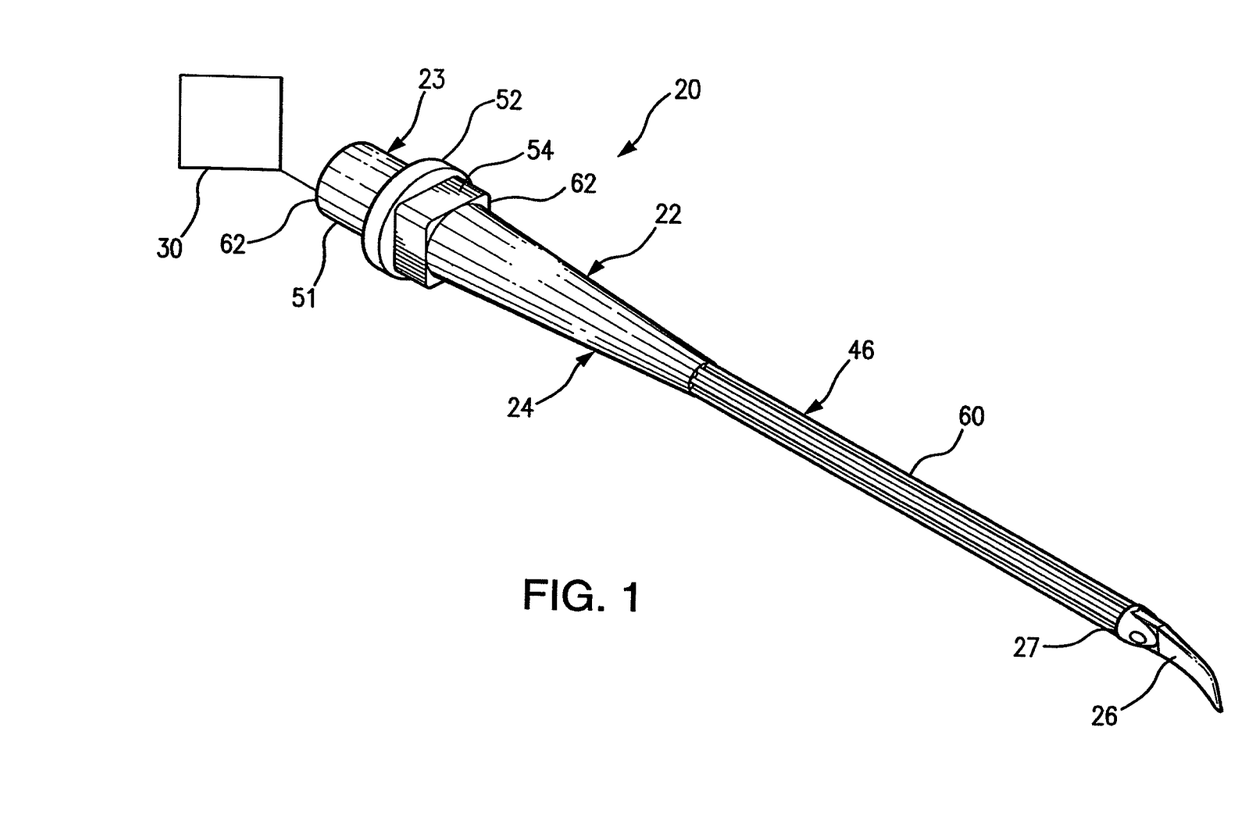
FIG. 1 illustrates a perspective view of a first embodiment of a phacoemulsification opthalmologic surgical instrument of the present invention.
Figures 2, 3:
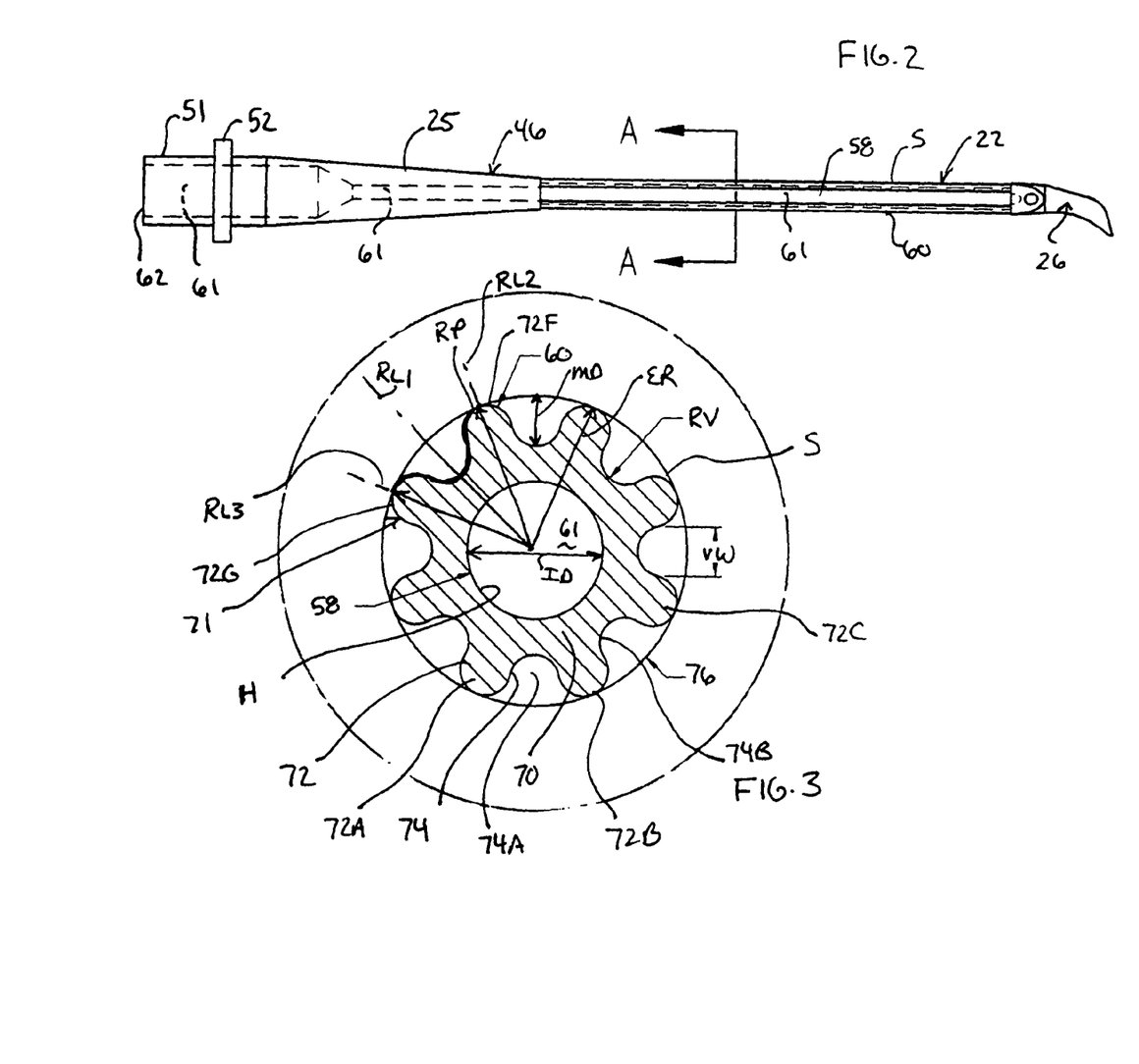
FIG. 2 illustrates a side elevational view of the instrument of FIG. 1 with the shaft section aspiration pathway (or lumen hole) and applicator tip's aspiration porting shown in dashed line.
FIG. 3 shows an enlarged cross-sectional view of the stem cross section taken along line A-A.

Phacoemulsification device 20 is shown in FIGS. 1 to 3 as including cutting device 22 (also referenced below as a knife, chopper and "ultrachopper") and, in this embodiment, also movement generator 30 shown schematically as being in movement communication with the connecting structure 23 of cutting device 22. Movement generator 30 provides, for example, means for ultrasonic vibration of applicator tip 26 and is preferably in the form of an ultrasonic vibrating device such as one utilizing a piezoelectric transducer, although alternate movement generating devices are also featured under the present invention including, for example, alone or in conjunction with one or the other, fluid, acoustic, motor (e.g., offset cam), reciprocating piston or other movement generating means.

Cutting device 22 comprises ultrasonic energy transmission section 24 and tip 26 with energy transmission section 24 comprising connecting structure 23 and shaft 46. In an exemplary embodiment shaft 46 includes a transition section 25 which is preferably a tapered or conical section 25 as well as a grooved, generally cylindrical shaft section 60. For example, in an exemplary embodiment transition section 25 features an inclination in relation to the horizontal axis of about 3 to 5 degrees (e.g., approximately 3.6 degrees) and preferably has a narrow distal diameter end (e.g., 1 mm) and a wider proximal end (e.g., 2 mm).

Shaft 46 is further shown as being a hollow shaft that has an axially extending lumen 58 forming part of an aspiration passageway 61. Shaft section 60 is preferably approximately 14 mm in length and 1 mm in diameter. Also, between the end points 62 and 27 of energy transmission section 24 there is found flange disk 52 (e.g., one that is about 2.5 mm (e.g., 2.62 mm) in diameter and with a width of approximate 0.5 mm) sandwiched between threaded cylindrical male projection tube 51 and square head 54 (e.g., a square of approximate 2*2 mm and 1 mm in thickness). It should be noted that all dimensions provided above and below throughout this application are not intended to be limiting, but of assistance in illustrating some of the possible characteristics of some of the embodiments of the invention including dimensions that, for example, are well suited for a surgeon positioning and utilizing the surgical instrument of the present invention within the limited space eye environment involved as well as providing a cutting device that is readily attachable to preexisting movement generators and irrigation systems. For instance, connector 48, with threaded male connection tube 51, flange disk 52 and square head 54, as well as step down conical transition shaft section 25 are also present in standard models of phacoemulsification devices, and thus the cutting device 22 of the present invention is well-suited for ready replacement of prior art cutting devices designed for securement to standard phacoemulsification handpieces. In other words, the illustrated male connection tube 51 with standard threaded proximal three thread rings on a supporting cylinder of approximately 2 mm in diameter and 4.65 mm in length is adapted for attachment to any one of a variety of phacoemulsification handpieces, many of which utilize a piezoelectric vibration source as an example of a vibration source.

In much of the prior art, when irrigation fluid circulation is utilized to help cool the vibrating cutting device and/or provide fluid circulation within the surgical area of the eye, there is typically utilized a sleeve, which is typically formed of a medical grade silicone and has a proximal sleeve segment with suitable connection for securement relative to the interior lumen. A feature of the present invention is a shaft with a high efficiency exterior cooling configuration that provides for sufficient cooling as to avoid having to use a sleeve at all thus providing a device free of a cooling sleeve about the shaft. This sleeveless arrangement further provides for the ability to make small cataract access eye incisions (e.g., less than 1.5 mm as in 1.1 mm incision) which small incision access would be precluded in situations where a cooling sleeve is utilized.

Figure 4:
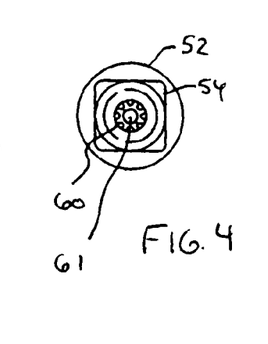
FIG. 4 shows a right end view of the cross section taken along line A-A.

FIGS. 3 and 4 illustrate the longitudinal groove and projection series combination 71 which feature projections 72 and valleys 74 that are respectively equally sized and spaced about the circumference of the shaft section 60. Further illustrated in FIG. 3 is the relative radial thickness differential relative to the lumen aspiration hole defined by interior lumen wall H. As also seen from FIG. 3, the projections 72 are rounded curved shaped projections with valleys 74 shown comprising similarly curved grooves or depressions. In other words, extending about aspiration passage 61 for the shaft section 60 is provided base section 70 having an interior preferably cylindrical cavity defined by wall H. Extending about base 70 in a sinusoidal series like fashion are bulbous projections 72 separated by valleys 74 of combination 71.

As seen from FIG. 3, for example, there is provided a generally sinusoidal projection and valley sequence relative to the exposed cross-sectional surface S for section 60. As further seen from FIG. 3, in this embodiment convoluted shaft section 60 features a series of equally spaced convex projections 72 (e.g., 72A, 72B, 72C . . . etc.) separated by equally spaced concave valleys or grooves 74 (e.g., 74A, 74B, etc). The outermost circumference for convoluted shaft section 60 is represented by the circle touching the outermost extreme point of each of projections 72 and is referenced as circumference 76 in FIG. 3. This circumference is also representative of the insertion reception size relative to the shaft section 60 when inserted/placed within the access incision made to gain access to the desired substrate for treatment (e.g., the eye incision made to gain access to a cataract). In an exemplary embodiment the diameter of circumference 76 is at about 1.0 mm or lower (e.g., a size that can be accommodated by the above described equal to or less than 1.5 mm incision as in the noted 1.1 mm incision size). In an embodiment of the invention the circumference is about 1.0 mm as, for example, 1.0 mm+/−0.2 mm or 1.0 mm+/−0.1 mm.

As further seen from FIG. 3, projections 72 are supported on a preferably cylindrical base body 70 having the aforementioned aspiration cavity 61 defined by wall H representing the interior surface of base body 70. As an example of an embodiment well suited for use in such micro-incisions of 1.5 mm or lower such as that 1.1 mm incision size, there is featured a 0.9 mm diameter for circumference 76 of shaft section 60. Thus for this exemplary embodiment, external circumference 76 has radius ER of 0.45. Also, for exemplary embodiments lumen 58 of the aspiration cavity 61 (defined by wall H) has a radius of about equal or less than the radial sum of the base body 70 and projection height for projections 72. For example, an exemplary embodiment features a 0.40 mm internal diameter ID which thus represents a radius of 0.20 mm relative to the overall radius of 0.45 for circumference 76. Accordingly, the sum of the base and projection radius extension is 0.25 mm versus the 0.2 mm radius for the interior aspiration port. Thus, the solid portion represented by base body 70 and projections 72 makes up about ½ (e.g., 56%) of the overall radial distance for circumference 76 while the interior aspiration porting represents the remainder with 44% being illustrative. That is, the relative radial length of the aspiration port is close to equal or less than that of the sum of the base body and projection radial extension (a differential of 12% as in the noted 44% lower value for the aspiration radial length compared to the 56% for the sum of the base body and projection radial extension).

FIG. 3 also shows that the contour of the projections preferably is a bulbous configuration with a convex upper region RP of the projections 72 having a radius of, for example, 0.07 mm. The valleys 74 are preferably provided with a generally opposing and corresponding concavity curvature to that of projections' convex curvature as in concave valley bases RV for valleys 74 having an equal value of curvature as that of the bulbous projections 72 (e.g., a radius as well of 0.07 mm). With reference to FIG. 3 there is seen that the valleys have a maximum circumferential width VW which is, for example equal to the diameter of the concavity RV or 2 times the above noted 0.07 curvature radius to provide a valley width VW of 0.14 mm. As still further seen by FIG. 3 an extension of the concave curvature positioned in the valley results in the maximum depth value of the valley relative to the outer circumference line 76 being equal to valley width WV or, as an example, a maximum depth MD of 0.14 mm.

The projections 72 are seen in the FIG. 3 embodiment as having a projection height off from the base body equal to the maximum valley depth (e.g., projections of 0.14 mm height. Accordingly the depth of the valleys (e.g., the noted 0.14 mm) is preferably at about 50% of the overall thickness of the base body 70 and radial extension of a projection. For example, the noted 0.25 thickness for the noted base body and projection 72 combination results in a base body having lesser radial thickness than the radial extension of the projections (e.g., 0.11/0.25 mm is lesser than 0.14/0.25 mm with the percentages being about 56% depth of valley versus 44% base body radial thickness).

In addition to valleys 74 extending relatively deep (e.g. greater than 50% of the overall, maximum radial thickness out from aspiration defining surface H), they also are shaped to have opposing (e.g., mirror image) "S" shaped side walls. That is, as seen from the radial line RL1 bisecting valley 74F and the radial lines RL2 and RL3 bisecting projections 72F and 72G there is provided an S-shaped surface extension from that RL1 to RL2 and then a corresponding mirror image S-shaped surface extension extending from RL1 to RL3 as represented by the thickened lines extending between those points. In the illustrated FIG. 3 embodiment there is featured an equal sized, shaped and spaced projection set and a corresponding equal sized, shaped and spaced valley set (e.g., 8 projections and 8 valleys illustrated).

Figures 5, 8:
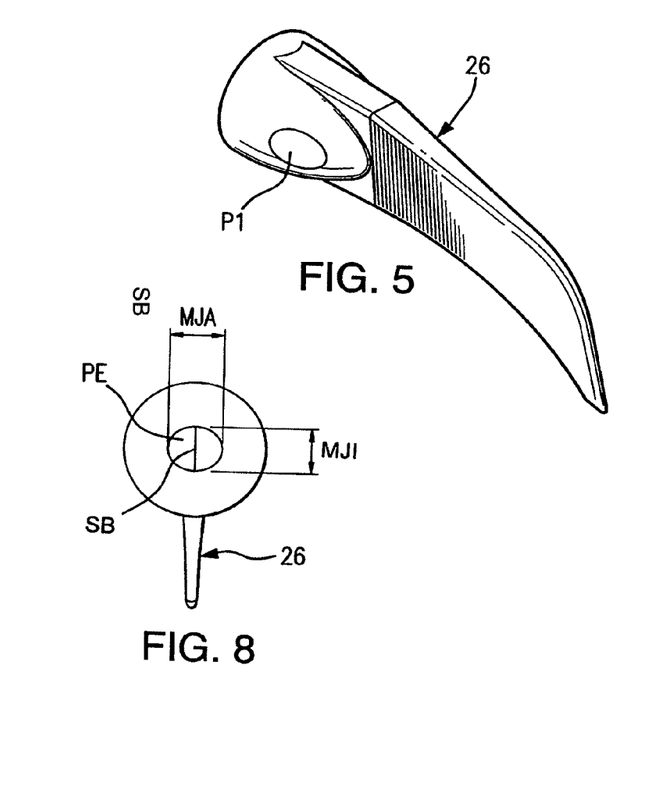
FIG. 5 shows a perspective view of the cutting tip shown in FIG. 1
FIG. 8 shows a left end view of the end of cutting tip shown in FIG. 5.
Figures 6, 7:
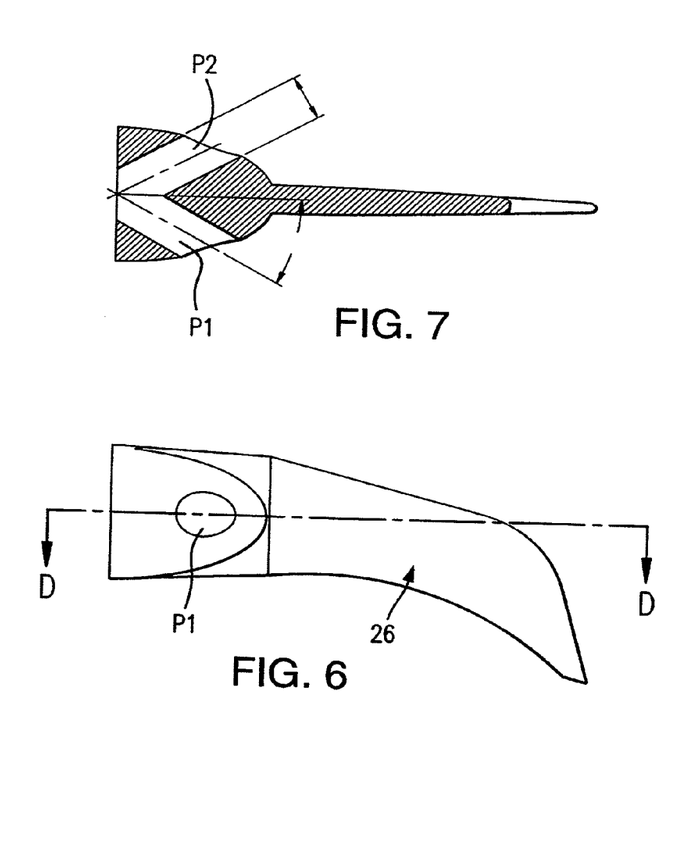
FIG. 6 shows a side elevational view of that shown in FIG. 5.
FIG. 7 shows a cross-section view taken along cross-sections line D-D in FIG. 6.

FIGS. 5 to 8 illustrate an embodiment of a cutting tip 26 that is well suited for use with the convoluted shaft section 60 of device 20 (as well as 20' described below) having the internal and centrally positioned lumen passageway 58. As seen the cutting tip 26 has a pair of aspiration inlet ports P1 and P2 that are preferably equally obliquely orientated relative to the central axis of extension of the aspiration conduit extending within convoluted shaft section 60. As seen there is featured an oblique angle of AN1 which in a preferred embodiment is about 30 degrees (each side) with a diverging arrangement in going from a proximal to distal extension direction for the cutting tip 26 (e.g., a monolithic component together with shaft 46 of the cutting device 22 or an integrated component). As also seen from FIG. 7 the diameter DP of each port is preferably the same as in about 0.3 mm. This arrangement results in the proximal end of the cutting tips aspiration passageway PE having an oblong configuration with a longer side to side length (major diameter axis) MJA and a shorter height minor diameter axis MJI for the oblong shape as shown in FIG. 8. This aspiration oval shaped outlet combination preferably opens into the distal end of the above described lumen conduit 58 encompassed by convoluted shaft section 60 (e.g., a 0.35 mm side to side major axis and a 0.3 mm vertically orientated minor axis. Thus the proximal end porting of the cutting head is less in size than the general 0.4 mm aspiration conduit formed within convoluted shaft section 60. There is provided either a sharp break SB (which is suitable in view of the one direction aspiration direction preferred for the illustrated embodiment) or there is provided a graduated border region between the aspiration conduit portions for convoluted section 61 and the cutting head 26.

Thus, FIGS. 5 to 8 show a preferred cutting tip 26 with a preferred porting design for use with the cooling stem 46 described above (e.g., shown separated but is preferably an integrated component of a monolithic device 20 formed of surgical steel or the like).

FIGS. 9 to 12 show an alternate embodiment 20' of a phacoemulsification opthalmologic surgical instrument or device having generally the same characteristics as described above but for a modified exterior shaft configuration 73 in the convoluted shaft section 60', which features a somewhat similar valley/projection arrangement but for the sides valleys being replaced with solid material to provide a generally solid side wall configuration albeit with smooth curvature border wall regions.

Figure 9:
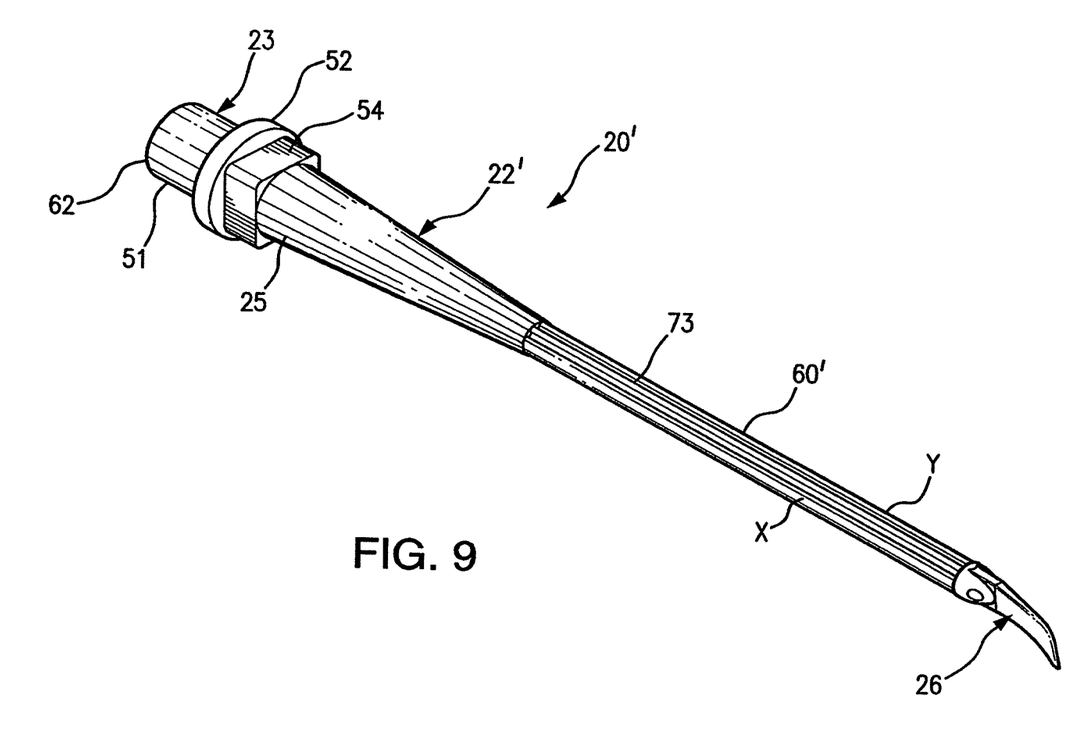
FIG. 9 illustrates a perspective view of a second embodiment of a phacoemulsification opthalmologic surgical instrument of the present invention.

For example, in the embodiment of FIGS. 9 to 12 there is featured a first set of projections 172A to 172D having a generally similar configuration as that for projections 72A of the first embodiment as well as side walls X and Y which are shown in FIG. 9 to extend generally parallel and to opposite sides relative to the central axis of elongation of the lumen 58. As further seen, from FIG. 11 solid wall side regions X and Y still feature a curved overall outer configuration with the radially exteriormost exposed surface of the projection RE shown conforming to the generally cylindrical circumferential extension around the tips of the projections) and from which extend side walls (SW2) which are preferably similar in configurations to the side walls SW1 extending off the first set of projections 172A to 172D.

Figures 10, 11:
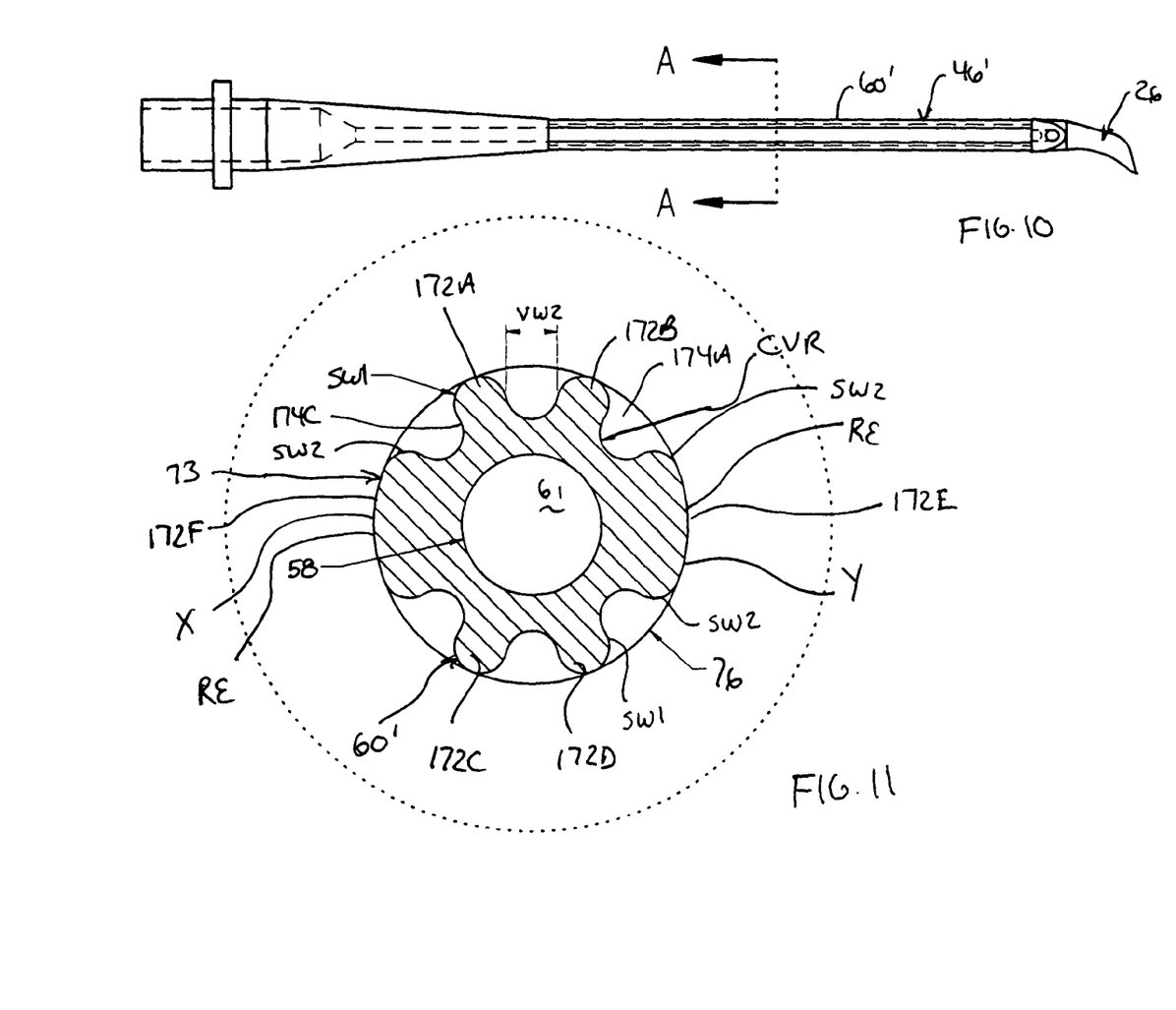
FIG. 10 illustrates a side elevational view of that shown in FIG. 9 with the porting and passageways shown in dashed line and with the stem shown in cut-away.
FIG. 11 shows an enlarged cross-sectional view of the stem taken along line A-A of FIG. 10.
Figure 12:
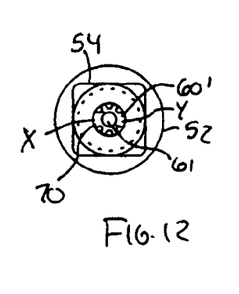
FIG. 12 shows a right end view of the cross section taken along line A-A in FIG. 10.

The side walls X and Y are representative of a second set of projections referenced as 172E and 172F in the illustrated embodiment. The outermost portion of curved line RE presents a central line (central being heightwise with the tip in cutting position) of each said wall X and Y which central line of each extends generally parallel to the central flow passageway defined by lumen 58 extending in shaft section 61'.

Also, as further shown in FIGS. 9 to 12, the porting in cutting tip 26 is in general longitudinal alignment (and generally in commensurate height relationship in the mid region of the shaft when the cutting tip is down) with the solid side wall extension. Further, the side wall positioning of the solid side walls provides for incision insertion and/or projection-retraction movement of the shaft with the ends of the incisions in contact with the smooth curvature and solid side walls as opposed to the groove/projection regions above and below those side walls.

As further shown in FIGS. 9 to 12 the overall exposed configuration 73 for shaft section 61 preferably comprises two side walls (one enlarged side wall projection to each side), two projections above those side walls which are separated by three intermediate valleys 174A, 174B and 174C with a mirror image projection/valley relationship below the side walls. Thus, in the first embodiment 20 there is preferably a total of 8 equally spaced projections and 8 equally spaced valleys (with the projections cross-sections preferably conforming to those of the grooves) and with the instrument 20' having 4 first set projections and the two side walls (or two second set projections) with a total of 6 grooves (again commensurate in cross-section with the first set projections but not the second set of projections) separating the projections and/or side walls from each other.

FIG. 11 provides an enlarged view of the cross-section configuration of convoluted shaft section 60'. The convoluted shaft section 60' of FIG. 11 is preferably provided with an overall outer diameter similar to that of the first described embodiment which is well suited for sleeveless application of the instrument during cataract chopping and/or aspiration stages (preferably both simultaneously). Further with the design of the first embodiment and of the second embodiment it is possible to carry out the standard cataract chopping procedures without an added cooling fluid sleeve as the configuration of the convoluted cross-section is designed for sufficient fluid cooling as to avoid harmful effects due to ultrasonic vibration heat up in the region of the incision border material and instrument interface.

As noted, the FIG. 11 embodiment includes an above and below set of bulbous projections 172 (e.g., 172A and 172B above and 172C and 172D below in the FIG. 11 embodiment) and the noted second, side positioned set of projections 172E and 172F. The first set and second set of projections preferably extend out as to provide a diameter of about 1 mm again for the outer circumference 176 (contacting tangentially the outermost points of projections 172) to render the instrument well suited for the smaller range of incision lengths described above. For example a 0.9 mm circumferential diameter 176 is well suited for many uses like that described above. The two upper projections or the first set have adjacent (intermediate and outer sides) valleys 174 (e.g., 174A, 174B and 17C) adjacent thereto. The relative shapes of the valleys and projections are similar to those above but for optionally a slightly larger valley concave radius CVR (e.g., 0.075 mm) and valley width VW2 (e.g., 0.15 mm) which is suited as well for the maximum depth of the valley and hence radial extension of the projections in the illustrated embodiments. Also the interior aspiration passageway 61 is preferably of a similar size and shape as that of the first embodiment (e.g., 0.4 mm diameter).

As further seen from FIG. 11 there is filled in (conceptually) the left and right valleys featured in the first embodiment from the side regions referenced as X and Y for the convoluted section 60'. This provides the longer circumferential extension RE as compared to the semi-circular in cross-section outer regions of the first set of projections. However, in the illustrated embodiment there is still provided a generally curved (no exposed edges) at the above and below surface sections of the side regions X and Y as shown by side wall SW2, for example.

In use, the instrument embodiments featured above can be readily inserted within the small incisions described above and used without an outer sleeve conduit that is designed in the prior art to provide a fluid cooling channel between the shaft of a phacoemulsification instrument and that sleeve. This sleeve arrangement is not required under preferred uses of the illustrated instrument embodiments 20 and 20'. Further once inserted the instrument can be used to breakdown a cataract and to aspirate portions of the broken down cataract through the aspiration port system described above. While a cutter head is shown in the illustrated embodiment the convoluted shaft sections such as 60 and 60' described above can be utilized in other instruments as in other tools (e.g. the cataract manipulation tools used in conjunction with the cutting knife or the like) utilized in association with a cataract removal treatment such as those described (and incorporated herein) in the prior art presented in the background of the present application inclusive of different applicator tips including more needle like ends. The streamlined shaft section embodiments of the present invention, such as those described above, are well suited for use in the context of ultrasonic vibration applications or in other situations where heat generation is of concern.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:
1. A phacoemulsification device, comprising:
   a shaft having a proximal end and a distal end;
   an applicator tip provided at the distal end;
   said shaft including an aspiration passageway extending within said shaft and said applicator tip having an aspiration port that is in flow communication with the aspiration passageway, and said shaft includes a shaft section having an exposed convoluted surface that extends longitudinally along said shaft section and, in cross-section, has a sinusoidal pattern; wherein, the exposed convoluted surface comprises a first set of projections and a second set of projections, with each projection presenting a curved surface at a radial outermost end; and the curved surfaces of the projections of the first set of projections are shorter than the curved surfaces of the projections of the second set of projections.

2. The device of claim 1 wherein said convoluted surface includes a plurality of longitudinally elongated valleys each with a concave base surface section, each valley positioned intermediate of two longitudinally extending projections, with each projection having a convex outermost surface section.

3. The device of claim 2 wherein the curvature of the convex outermost surface section of at least some of the projections is equal to the curvature of the concave base surface section of at least some of the valleys.

4. The device of claim 2 wherein two times a radius value for the concave base surface curvature is equal to the maximum depth of each valley down from a circumferential line which contacts the outermost points of said first and second sets of projections.

5. The device of claim 2 wherein said longitudinally elongated valleys and projections are linearly arranged as to extend parallel to a central axis of extension of said shaft section, and said aspiration passageway extends along that central axis of extension, and the aspiration passageway being in fluid communication with two independent aspiration ports which extend obliquely out from the aspiration passageway.

6. The device of claim 2 wherein said shaft section includes a base body having an interior surface defining the aspiration passageway and an exterior surface which defines the radially interior most points of the concave base surface sections of said valleys, and said first and second sets of projections extending radially off said base body to about an equal amount or greater extent than the radial thickness of said base body.

7. The device of claim 1 wherein said exposed convoluted surface is configured as to be free of any sharp edges and wherein said applicator tip comprises a blade section and a tapered transition section having a maximum circumference corresponding to a circumferential line contacting the radial outermost end of said first and second sets of projections, and said transition section converging in a distal direction to a proximal end of said blade section, and wherein said first and second sets of projections extend to a proximal end of said transition section.

8. The device of claim 1 wherein a circumferential width of an intermediate in height region of at least some of said projections is about equal to the circumferential width of an adjacent valley.

9. The device of claim 1 wherein the convoluted surface comprises valleys positioned intermediate of adjacent projections, with each projection and each valley of the exposed convoluted surface of the shaft section linearly arranged as to extend parallel to a central axis of extension of said shaft section, along the entire length of said shaft section.

10. The device of claim 9 wherein all of the valleys have a common cross-sectional configuration about the entire circumference of said shaft section.

11. The device of claim 1 wherein said curved surfaces of said first and second sets of projections define a circumferential surface at the radial outermost end of said first and second sets of projections, and projections in said second set of projections have a circumferential surface that is circumferentially longer than the circumferential surface presented by projections in said first set of projections, and all projections in said first and second sets have curved side wall edge regions that extend down and away from the radial outermost end of the respective projections.

12. The device of claim 11 wherein said first set of projections includes projections that are positioned, when the device is in use, in both an upper and lower region of the exposed convoluted surface of said shaft section, and wherein said projections of said second set are positioned, when the device is in use, to left and right regions of the exposed convoluted surface of said shaft section.

13. The device of claim 11 wherein each projection of said second set of projections have a configuration represented by taking a pair of projections in said first set of projections and an associated valley therebetween and filling in that associated valley up to a circumferential line that extends between radial outermost points of the pair of projections in said first set of projections.

14. The device of claim 1 wherein a circumferential line extending into contact with a radial outermost point of said first and second sets of projections is about 1 mm or less in diameter.

15. The device of claim 14 wherein
the convoluted surface comprises valleys positioned intermediate of adjacent projections,
the aspiration passageway is defined by an internal surface of said shaft section which has a radius of about 45% relative to the radius of the circumferential line, and
said shaft section is comprised of a base body off from which said first and second sets of projections radially extend outward, with said valleys having a maximum depth that represents about 55% of the radial distance from said internal surface to said circumferential line.

16. A method of removing a cataract, comprising
inserting the device of claim 1 into an incision formed in an eye of less than 1.5 mm such that projections of the convoluted exposed surface come into direct contact with wall segments of the eye defining the incision, and subjecting said device to vibration.

17. The method of claim 16 wherein the device insertion incision is 1.2 mm or less and there is further provided a cooling fluid irrigation source incision that is separate and apart from the device insertion incision, and wherein said device comprises a connection hub at the proximal end suited for attachment with a phacoemulsification movement generator.

18. The phacoemulsification device of claim 1, wherein the applicator tip is dimensioned for insertion into an eye and into contact with a cataract and said shaft has a phacoemulsification movement generator connector end at a proximal location and an applicator tip supporting end at a distal end, and wherein said shaft section extends in a region positioned between said proximal and distal ends of said shaft, and said exposed convoluted surface includes longitudinally extending projections and longitudinally extending valleys arranged in sequence about the circumference of the shaft section, and wherein the projections and valleys have smooth sloped curving walls in cross section and which smooth sloped curving walls include a plurality of mirror image S-shaped regions extending from a maximum radial extension region of a first projection, down to a maximum depth valley region of a first valley and up to a maximum radial projection of a second projection, with said valley region being positioned between respective first and second projections.

19. The device of claim 18 wherein said cross section of said convoluted surface has a diameter that is about 1 mm or less.

20. The device of claim 19 wherein said curved surfaces of said projections in said first and second sets of projections define a circumferential surface at the radial outermost end of said first and second sets of projections, and projections in said second set of projections have a circumferential surface that is circumferentially longer than the circumferential surface presented by projections in said first set of projections, and all projections in said first and second sets have curved side wall edge regions that extend down and away from the radial outermost end of the respective projections.

21. The device of claim 20 wherein said first set of projections includes projections that present a semi-circular radially outermost region and said first set of projections are positioned, when the device is in use, in both an upper and lower region of the exposed convoluted surface of said shaft section, and wherein said second set of projections are positioned, when the device is in use, to left and right regions of the exposed convoluted surface of said shaft section.

22. The phacoemulsification device of claim 1 further, comprising,
a movement generator connector, with said shaft extending between the applicator tip and the movement generator connector, and said exposed convoluted surface includes longitudinally extending projections and longitudinally extending valleys arranged in sequence about the circumference of the shaft section, and wherein the projections have smooth sloped curving walls in cross section as to avoid sharp edge presentment about the circumference of the convoluted exposed surface of the shaft section.

23. The device of 22 wherein said valleys and said projections of said first and second sets are entirely comprised of curved surface sections.

24. The device of claim 22 further comprising a phacoemulsification movement generator connected with said movement generator connector which is provided at the proximal end of said shaft.

25. The device of claim 22 wherein said curved surfaces of said projections of said first and second sets of projections define convex surfaces at the radial outermost end of said projections, with the projections of the first set of projections having a smaller convex curvature radius as compared to the convex curvature radius of the projection of the second set of projections.

26. The device of claim 25 wherein a horizontal plane extending through a central region in height of the projections of said second set of projections also extends through a port hole access opening of the aspiration port provided in said applicator tip.

27. A phacoemulsification device, comprising:
a shaft having a proximal end and a distal end;
an applicator tip provided at the distal end;
said shaft including an aspiration passageway extending within said shaft and said applicator tip having an aspiration port that is in flow communication with the aspiration passageway, and said shaft includes a shaft section having an exposed convoluted surface that extends longitudinally along said shaft section and, in cross-section, has a sinusoidal pattern; wherein,
the exposed convoluted surface comprises a first set of projections and a second set of projections, with each projection presenting a curved surface at a radial outermost end;
the curved surfaces of the projections of the first set of projections are shorter than the curved surfaces of the projections of the second set of projections; and
said curved surfaces of said first and second sets of projections present a generally semi-circular outermost exposed surface, such that each projection comprises a radial outermost point corresponding to a common circumferential line, wherein projections of said second set of projections have an outermost exposed surface presentation that is circumferentially longer than an outermost exposed surface presentation of projections of said first set of projections, and wherein all projections in said first and second sets have curved side wall edge regions that extend down and away from the curved outermost exposed surface presentations of the respective projections.

28. The device of claim 27 wherein said first set of projections includes projections that are positioned, when the device is in use, in both an upper and lower region of the exposed convoluted surface of said shaft section, and wherein said projections of said second set are positioned, when the device is in use, to left and right regions of the exposed convoluted surface of said shaft section.

29. A phacoemulsification device, comprising:
a shaft having a proximal end and a distal end;
an applicator tip provided at the distal end;
said shaft including an aspiration passageway extending within said shaft and said applicator tip having an aspiration port that is in flow communication with the aspiration passageway, and said shaft includes a shaft section having an exposed convoluted surface that extends longitudinally along said shaft section and, in cross-section, has a sinusoidal pattern; and
said applicator tip includes a cutter tip with an opposing flat faced side walls section, having a pair of inlet ports positioned on opposite sides of said opposing flat faced side walls section such that said inlet ports extend in converging fashion into fluid communication connection with the aspiration passageway, and wherein said inlet ports converge into a common, coinciding outlet port, being oblong in cross section, that feeds directly into the aspiration passageway;
wherein said opposing flat faced side walls section comprises a pair of opposing flat faced side walls at a distal end and a transition section at a proximal end, and said inlet ports are positioned on opposite sides of said transition section.

30. The device of claim 29, wherein said convoluted surface comprises projections and grooves, and said transition section is a tapered transition section having a proximal end with a maximum circumference line corresponding to a circumferential defined by a radial outermost end of said projections, with said projections and grooves being elongated and extending to said proximal end of said transition section, and said tapered transition section converging in a distal direction to correspond with a proximal end of said opposing flat faced side walls section of said cutter tip.

* * * * *